United States Patent
Fujiwara et al.

[11] Patent Number: 5,966,676
[45] Date of Patent: *Oct. 12, 1999

[54] CALIBRATION-INABILITY WARNING METHOD IN ANALYZING APPARATUS

[75] Inventors: Masahiko Fujiwara; Kiyomi Shiotani, both of Miyanohigashi-machi, Japan

[73] Assignee: Horiba Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/670,567

[22] Filed: Jun. 26, 1996

[30] Foreign Application Priority Data

Jul. 1, 1995 [JP] Japan ................................. 7-187776

[51] Int. Cl.$^6$ ................................................. G01N 21/61
[52] U.S. Cl. .............................. 702/85; 702/30; 73/1.05; 250/252.1
[58] Field of Search ......................... 364/571.01, 571.02, 364/571.04, 497, 571.07; 73/1 R, 1 G, 863.83, 863.33, 863.03, 1.05, 1.07; 423/219; 422/67; 436/50; 324/601; 250/252.1, 343, 282, 382; 702/24, 30, 27, 87, 88, 85

[56] References Cited

U.S. PATENT DOCUMENTS 5,608,212  3/1997  Merilainen et al. .................. 250/252.1

OTHER PUBLICATIONS

W. Olsowski. "Automatisches Kalibriersystem fur Betriebsanalysengerate"; Technisches Messen TM. 53. Jahrgang Heft Jan. 1986.

*Primary Examiner*—Kamini Shah
*Attorney, Agent, or Firm*—Oppenheimer Wolff & Donnelly LLP

[57] ABSTRACT

A calibration-inability warning method in an analyzing apparatus determines in advance when the analyzing apparatus approaches a calibration-inability condition prior to entering calibration inability condition. To do so, coefficient ranges are set, and a calibration coefficient is computed. It is then determined whether the calibration coefficient is within a normal calibration range, a calibration-inability range, or a normal calibration range with no allowance. Signals are generated indicating that the calibration-inability condition is approaching when the calibration coefficient becomes a certain value in the vicinity of the calibration-inability range.

7 Claims, 2 Drawing Sheets

CALIBRATION-INABILITY WARNING METHOD IN ANALYZING APPARATUS

BACKGROUND OF THE INVENTION

1. Field of the Invention

The invention relates to a calibration-inability warning method in an analyzing apparatus.

2. Description of the Related Art

Hitherto, for example, in a gas analyzing apparatus, with respect to its sensitivity degradation, errors of the measured values are calibrated at regular intervals by a processor unit such as a computer and the like. If the calibration coefficient determined by computations is within the normal calibration range as shown in FIG. 4, the result, provided that the calibration is normally completed, is outputted. At the same time the calibration coefficient is updated. If the calibration coefficient is outside the calibration range, calibration inability is outputted as ALARM signal to enable repair and adjustment of the analyzing apparatus.

However, even when the sensitivity of the analyzing portion gradually degrades and the calibration coefficient approaches the calibration-inability range, it is not able to be determined, and suddenly a calibration-inability condition exists. The causes for the inability condition must be located, and replacement parts must be procured once such a condition comes into existence. Further, there is apprehension and uncertainty that the reliability of measured values is lost until the repair or the adjustment of the analyzing apparatus has been completed.

Under present circumstances, users dispose of this situation as missing of the measured value (missing data) and failure of the analyzing apparatus. However, in particular with pollution control instruments, the concentration output is sent to a specified control section (for example, government agencies) by a telemeter, and the above-mentioned missing data due to calibration inability may cause serious problems.

SUMMARY OF THE INVENTION

The invention is accomplished with the above-mentioned matters taken into account, and it is an object of this invention to provide a calibration-inability warning method in an analyzing apparatus which can check in advance that the analyzing apparatus approaches the calibration-inability condition before the analyzing apparatus actually enters the calibration-inability condition.

In order to achieve the above-mentioned object, the calibration-inability warning method in the analyzing apparatus according to the invention comprises (1) a process for setting coefficient ranges such as whether a computed calibration coefficient is within a normal calibration range when calibration is carried out, whether the calibration coefficient is within a calibration-inability range, or whether the calibration coefficient is within a normal calibration range without allowance, and (2) a process for generating signals indicating that a calibration-inability condition is approaching when the value of the calibration coefficient approaches the calibration-inability range. For example, let $K_Z$ be the zero calibration coefficient in the analyzing apparatus, with the following judgment criteria being set:

(1) normal when $-100.0 \leq K_Z \leq 100.0$;
(2) calibration inability when $K_Z < -200.0$ or $K_Z > 200.0$; and
(3) calibration-inability condition approaching and special care required when $-200.0 \leq K_Z < -100.0$ or $100.0 < K_Z \leq 200.0$.

In carrying out calibration, if the zero calibration coefficient compiled at the processor unit (such as a computer) is located in the range shown in Item 3, a CAUTION signal is outputted to call the attention of the operator of the analyzing apparatus. By doing so, the analyzing apparatus can be maintained by the user before calibration inability exists, and the missing-data time can be shortened. Because it also becomes possible to prepare for maintenance, such as procurement of parts, before calibration inability occurs, disposition after the occurrence of calibration inability can be carried out quickly.

DETAILED DESCRIPTION OF THE PREFERRED EMBODIMENT

Figure 1:
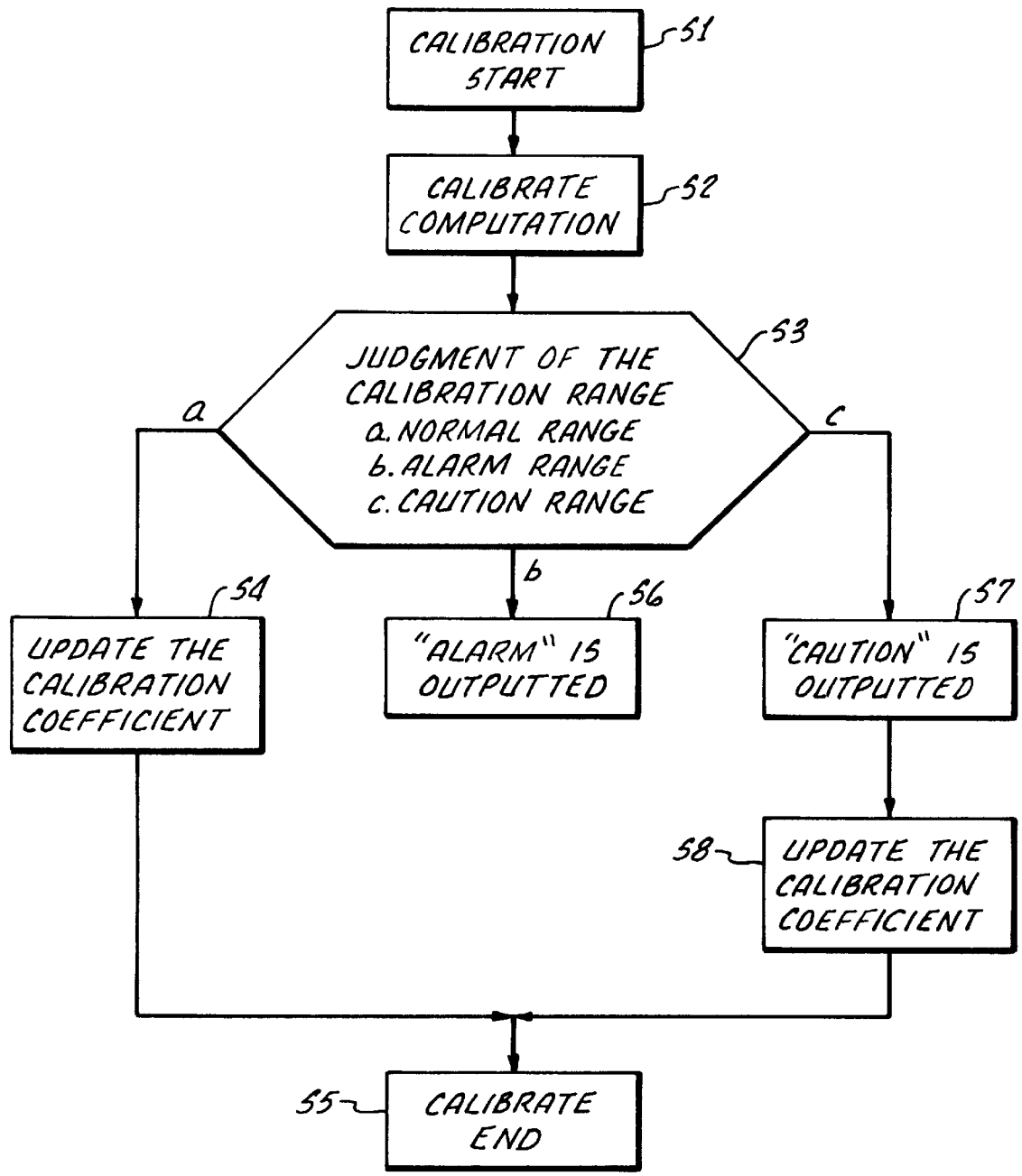
FIG. 1 is a flow chart illustrating a calibration-inability warning method in an analyzing apparatus according to the invention.

Referring now to the drawings, the present invention will be described in detail hereinafter.

Figure 2:
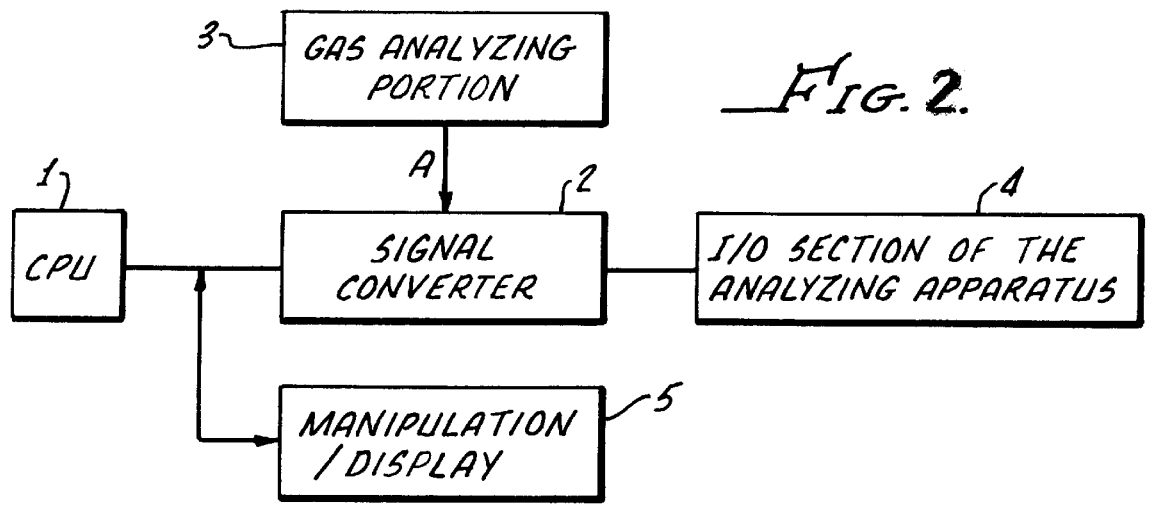
FIG. 2 is a block diagram illustrating the construction of an analyzing apparatus to which the method of the invention may be applied.

FIG. 2 schematically shows the construction of an apparatus, for example, a gas analyzing apparatus, to which the calibration-inability warning method is applied in the analyzing apparatus according to the invention. Numeral 1 is a computer functioning as a processor. Numeral 2 is a signal converter which comprises, for example, an analog-to-digital (AD) converter circuit or a digital-to-analog (DA) converter circuit. Numeral 3 is a gas analyzing portion, a sensor output A which is converted from analog to digital at the signal converter 2 and received by the computer 1. Numeral 4 is an input/output (I/O) section of the analyzing apparatus, where range signals as well as signals inputted from the outside, such as calibration, start, etc., are received by the computer 1 via the signal converter 2, and where range indications as well as signals, such as ALARM, CAUTION, etc., are outputted. Numeral 5 is a manipulation/display section of the gas analyzing apparatus, to which input keys and concentration indicators are provided.

Figure 3:
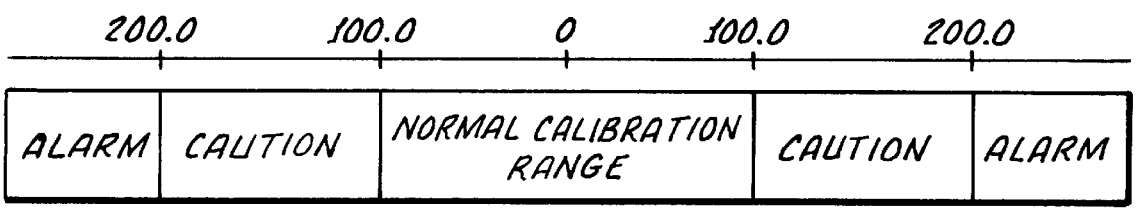
FIG. 3 is a diagrammatic representation which shows one example of the judgment criteria of the zero calibration coefficient range.
Figure 4:
FIG. 4 is a drawing for a schematic representation illustrating a conventional technique according to prior art.

In the gas analyzing apparatus, $K_Z$ represents a zero calibration coefficient. A judgment criteria range of the zero calibration coefficient $K_Z$ is shown in FIG. 3. For example, the following ranges may be present:

(1) normal when $-100.0 \leq K_Z \leq 100.0$;
(2) calibration inability when $K_Z < -200.0$ or $K_Z > 200.0$;
(3) state requiring caution because calibration inability condition is nearly reached when $-200.0 \leq K_Z < -100.0$ or $100.0 < K_Z \leq 200.0$.

Referring to FIG. 1, operation in the gas analyzing apparatus is described as follows.

The gas analyzing apparatus enters a calibration mode and calibration begins (step S1). The zero calibration coefficient $K_Z$ is computed in computer 1 (step S2). Judgment is made on whether the processed zero calibration coefficient $K_Z$ is in (1) a normal range, (2) a calibration-inability range, or (3) a caution state in which the calibration-inability state is approaching (step S3).

When the zero calibration coefficient $K_Z$ is located in the normal range, the calibration coefficient is updated as is (step S4), and calibration is completed (step S5).

When the zero calibration coefficient $K_Z$ is located in the calibration-inability range, an ALARM signal is outputted (step S6), and calibration is stopped (step S5). In this case, repair and adjustment may take place.

When the zero calibration coefficient $K_Z$ is located in the caution range, a CAUTION signal is outputted (step S7), the calibration coefficient is updated as is (step S8), and calibration is completed (step S5). In this event, since CAUTION is outputted, the attention of the operator of the gas analyzing apparatus is called, enabling the operator to maintain the gas analyzing apparatus before calibration inability occurs and shortening the missing-data time. Because the operator can prepare for maintenance, such as procurement of parts, before calibration inability occurs, the operator can quickly dispose of the situation when calibration inability actually occurs. In addition, because it is possible to confirm when the caution state is reached from the normal range to the calibration-inability range, it is possible to foresee when calibration inability will occur.

In the above-mentioned embodiment, the range of the zero calibration coefficient $K_Z$ is determined during calibration processing of the gas analyzing apparatus. However, the invention is not limited to this but may be designed to determine the range of the span calibration coefficient or interference correction coefficient. Further, the invention can be applied not only to a gas analyzing apparatus but also to other analyzing apparatuses.

As described above, according to the invention, it is possible to confirm that the analyzing apparatus is approaching the calibration inability state before such state occurs. Consequently, routine maintenance can be performed on the analyzing apparatus before calibration inability occurs, and the missing-data time or down time can be shortened. Because it is possible to prepare for maintenance, such as parts procurement, before calibration inability occurs, disposition can be quickly carried out when calibration inability actually occurs. It is also possible to foresee when calibration inability would occur.

What is claimed is:

1. A calibration-inability warning method for use in a gas analyzer, the method comprising the steps of:
   a) providing the gas analyzer with a gas analyzing portion equipped with an auto-calibrator set to calibrate at a specified time period, wherein the auto-calibrator compensates for a sensitivity degradation of the gas analyzing portion;
   b) setting a plurality of coefficient ranges including a normal range, a cautionary range, and an inability range indicative of when a calibration of the gas analyzer is unable to be performed, the cautionary range being positioned between the normal range and the inability range;
   c) computing a calibration coefficient;
   d) determining in which the coefficient ranges the calibration coefficient is located; and
   e) generating a signal when the calibration coefficient is in the cautionary range to indicated that the calibration coefficient is approaching the inability range.

2. The calibration-inability warning method of claim 1 wherein:
   the cautionary range includes:
     an upper cautionary range which is greater than an upper limit of the normal range; and
     a lower cautionary range which is less than a lower limit of the normal range; and
   the inability range includes:
     an upper inability range which is greater than an upper limit of the upper cautionary range; and
     a lower inability range which is less than a lower limit of the lower cautionary range.

3. The calibration-inability warning method of claim 1 wherein the normal range is evenly distributed about zero.

4. A gas analyzer having a warning apparatus for warning a user when a calibration coefficient approaches a calibration-inability range, the gas analyzer comprising:
   a gas analyzing portion having an auto-calibrator set to calibrate at a specified time period, wherein the auto-calibrator compensates for a sensitivity degradation of the gas analyzer portion;
   a signal converter connected to the gas analyzing portion for receiving data from the gas analyzing portion;
   a processor connected to the signal converter for computing the calibration coefficient from the data received from the gas analyzing portion, and for determining whether the calibration coefficient is in a normal range, a cautionary range, or a calibration-inability range, the cautionary range being positioned between the normal range and the calibration-inability range, the calibration-inability range being a range in which the warning apparatus is unable to calibrate the gas analyzing portion; and
   an input/output interface in communication with the processor for outputting a range signal when the calibration coefficient is located in the cautionary range, thereby indicating the approach of the calibration-inability range.

5. A method for generating a warning message in a gas analyzer in case of malfunction of an automatic calibration, the method comprising the steps of:
   specifying a time period for automatically calibrating the gas analyzer, wherein the automatic calibration compensates for a sensitivity degradation of the gas analyzer;
   computing a calibration coefficient during the calibration of the gas analyzer;
   setting coefficient ranges which indicate whether said calibration coefficient is within a normal calibration range in which the calibration is able to be performed for the gas analyzer, or within a calibration inability range in which the calibration is unable to be performed for the gas analyzer; and generating a signal when said calibration coefficient is within a cautionary range which is within said normal calibration range, said signal indicative of when said calibration coefficient approaches said calibration inability range.

6. The method of claim 5, wherein said cautionary range is set such that said cautionary range is reached first by a drifting calibration coefficient before said calibration coefficient enters said calibration inability range.

7. The method of claim 5 wherein the calibration of the gas analyzer is carried out when said calibration coefficient is within said cautionary range.

* * * * *